United States Patent
Schubert et al.

(10) Patent No.: US 8,658,849 B2
(45) Date of Patent: Feb. 25, 2014

(54) PROCESS FOR THE SEPARATION OF UNBRANCHED HYDROCARBONS FROM THEIR BRANCHED ISOMERS

(75) Inventors: Markus Schubert, Ludwigshafen (DE); Ulrich Mueller, Neustadt (DE); Christoph Kiener, Weisenheim am Sand (DE); Ingo Richter, Schwetzingen (DE); William Dolan, Yardley, PA (US); Frank Poplow, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 822 days.

(21) Appl. No.: 12/668,436

(22) PCT Filed: Jun. 30, 2008

(86) PCT No.: PCT/EP2008/058379
§ 371 (c)(1), (2), (4) Date: Jan. 11, 2010

(87) PCT Pub. No.: WO2009/007267
PCT Pub. Date: Jan. 15, 2009

(65) Prior Publication Data
US 2010/0197990 A1  Aug. 5, 2010

(30) Foreign Application Priority Data
Jul. 10, 2007 (EP) .................................... 07112154

(51) Int. Cl.
*C07C 7/13* (2006.01)

(52) U.S. Cl.
USPC ............. 585/830; 585/820; 95/143; 210/767; 208/310 R

(58) Field of Classification Search
USPC .................... 585/830, 820; 502/400, 152–157
See application file for complete search history.

(56) References Cited

U.S. PATENT DOCUMENTS 3,700,589 A  10/1972  Symoniak et al.
(Continued)

FOREIGN PATENT DOCUMENTS

EP  0 200 260  12/1986
(Continued)

OTHER PUBLICATIONS

Kyo Sung Park et al., "Exceptional chemical and thermal stability of zeolitic imidazolate frameworks," Jun. 23, 2006, PNAS 2006 vol. 103 pp. 10186-10191.*

(Continued)

*Primary Examiner* — Tam M. Nguyen
*Assistant Examiner* — Candace R Chouinard
(74) *Attorney, Agent, or Firm* — Oblon, Spivak, McClelland, Maier & Neustadt, L.L.P.

(57) ABSTRACT

The present invention relates to a process for the separation of at least one unbranched C4-C20 hydrocarbon from a fluid mixture containing the unbranched hydrocarbon and at least one branched isomer of the unbranched hydrocarbon, which comprises the step of—contacting the fluid mixture with an adsorbent comprising a porous metal organic framework material, which material comprises at least one at least bidentate organic compound coordinately bound to at least one metal ion, to get the unbranched hydrocarbon adsorbed, wherein the at least one at least bidentate organic compound is a monocyclic, bicyclic or polycyclic ring system which is derived from at least one heterocycle selected from the group consisting of pyrrole, alpha-pyridone and gamma-pyridone and has at least two ring nitrogens and is unsubstituted or bears one or more substituents selected independently from the group consisting of halogen, $C_{i\text{-}6}$-alkyl, phenyl, $NH_2$, $NH(C_{1\text{-}6}\text{-alkyl})$, $N(C_{1\text{-}6}\text{-alkyl})_2$, OH, Ophenyl and $OC_{i\text{-}6}$-alkyl, where the substituents $C_{i\_6}$-alkyl and phenyl are unsubstituted or bear one or more substituents selected independently from the group consisting of halogen, $NH_2$, $NH(C_{1\text{-}6}\text{-alkyl})$, $N(C_{1\text{-}6}\text{-alkyl})_2$, OH, Ophenyl and $OC_{i\text{-}6}$-alkyl. The present invention also relates to the use of said porous metal-organic framework material in a process for the separation of unbranched hydrocarbons from their branched isomers.

9 Claims, 3 Drawing Sheets

(56) References Cited

U.S. PATENT DOCUMENTS

Figure 1:
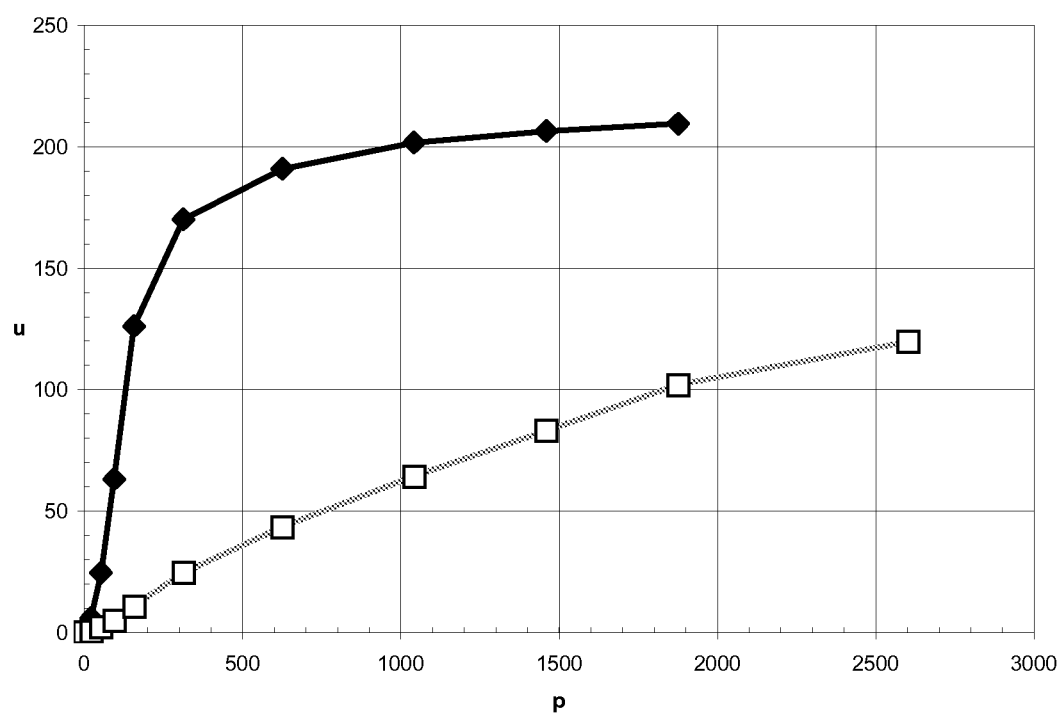

| | | | |
|---|---|---|---|
| 6,022,398 | A | 2/2000 | Cho et al. |
| 7,556,673 | B2 | 7/2009 | Schubert et al. |
| 2007/0099299 | A1 | 5/2007 | Simon et al. |
| 2008/0188677 | A1 | 8/2008 | Schubert et al. |
| 2008/0227634 | A1 | 9/2008 | Muller et al. |
| 2008/0281116 | A1 | 11/2008 | Schubert et al. |
| 2008/0300387 | A1 | 12/2008 | Schubert et al. |
| 2009/0032023 | A1 | 2/2009 | Pastre et al. |
| 2009/0042000 | A1 | 2/2009 | Schubert et al. |
| 2009/0092818 | A1 | 4/2009 | Kiener et al. |
| 2009/0133576 | A1 | 5/2009 | Schubert et al. |
| 2009/0171107 | A1 | 7/2009 | Puetter et al. |
| 2009/0183996 | A1 | 7/2009 | Richter et al. |
| 2009/0198079 | A1 | 8/2009 | Schubert et al. |
| 2009/0281341 | A1 | 11/2009 | Schubert et al. |
| 2009/0306420 | A1 | 12/2009 | Schubert et al. |
| 2010/0029476 | A1 | 2/2010 | Trukhan et al. |

FOREIGN PATENT DOCUMENTS

| | | |
|---|---|---|
| EP | 0 389 041 | 9/1990 |
| EP | 0 592 050 | 4/1994 |
| WO | 94 13584 | 6/1994 |
| WO | 94 29408 | 12/1994 |
| WO | 95 19222 | 7/1995 |
| WO | 2005 049892 | 6/2005 |
| WO | 2007 131955 | 11/2007 |

OTHER PUBLICATIONS

Hans-Jorg Bart and Ulrich von Gemmingen, "Adsorption," Jan. 15, 2005, Ullmann's Encyclopedia of Industrial Chemistry, Wiley-VCH, p. 5.*
U.S. Appl. No. 13/002,612, filed Jan. 4, 2011, Leung, et al.
U.S. Appl. No. 13/003,839, filed Jan. 12, 2011, Schubert, et al.
U.S. Appl. No. 12/863,339, filed Jul. 16, 2010, Schubert, et al.
Barcia, Patrick S. et al., "Kinetic Separation of Hexane Isomers by Fixed-bed Adsorption with a Microporous Metal-Organic Framework", The Journal of Physical Chemistry B, Letter, vol. 111, No. 22, pp. 6101-6103, (May 15, 2007).
Chen, Banglin et al., "A Microporous Metal-Organic Framework for Gas-Chromatographic Separation of Alkanes", Angew. Chem. Int. Ed., vol. 45, pp. 1390-1393, (2006).
Huang, Xiao-Chun et al., "Ligand-Directed Strategy for Zeolite-Type Metal-Organic Frameworks: Zinc(II) Imidazolates with Unusual Zeolitic Topologies", Angew. Chem, vol. 118, pp. 1587-1589, (2006).
U.S. Appl. No. 12/063,522, filed Feb. 11, 2008, Schubert, et al.
U.S. Appl. No. 12/161,024, filed Jul. 16, 2008, Schubert, et al.
U.S. Appl. No. 12/294,789, filed Sep. 26, 2008, Schubert, et al.
U.S. Appl. No. 12/447,671, filed Apr. 29, 2009, Schubert, et al.
U.S. Appl. No. 12/521,337, filed Jun. 26, 2009, Schubert, et al.
U.S. Appl. No. 12/594,727, filed Dec. 30, 2009, Mueller, et al.
U.S. Appl. No. 12/594,604, filed Oct. 5, 2009, Stein, et al.
U.S. Appl. No. 12/597,616, filed Dec. 4, 2009, Schubert, et al.

* cited by examiner

PROCESS FOR THE SEPARATION OF UNBRANCHED HYDROCARBONS FROM THEIR BRANCHED ISOMERS

The present invention relates to a process for the separation of at least one unbranched $C_4$-$C_{20}$ hydrocarbon from a fluid mixture containing the unbranched hydrocarbon and at least one branched isomer of the unbranched hydrocarbon.

Branched and unbranched hydrocarbons, such as n-butane and isobutane are important starting materials for technical applications and chemical reactions like the catalytic dehydrogenation resulting in the respective alkenes.

However, not for all applications it is desired to have these isomers in a mixture so that it is necessary to separate them from each other.

The selective adsorption of one of these isomers is a suitable procedure known in the art. Known adsorbing materials are zeolites or molecular sieves.

For example in U.S. Pat. No. 6,022,398 the high purity isobutane adsorption seraration and purification is described using an adsorption bed packed with zeolite 5 A.

Further zeolite based adsorbents and molecular sieves are described by V. Ya. Nikolina et al., Russian Chemical Reviews 29 (1960), 509-521 and D. Caputo et al., Separation Science and Technology 39 (2005), 1547-1561.

In recent times more effective adsorbents are described, which are called metal-organic framework materials.

B. Chen et al., Angew. Chem. 118 (2006), 1418-1421 describe the use of a zinc based metal-organic framework material, wherein the double organic linker system BDC and 4,4'-Bipy is used. This metal-organic framework material is called MOF-508a.

An analogous double organic linker constituted metal-organic framework material is described by L. Pan et al., Chem. 118 (2006), 632-635. The two linkers are 4,4'-(hexafluoroisopropylidene)bis(benzoic acid) and a pyridine derivative.

The metal-organic framework materials described for the aforementioned separation are very complex and unstable compared to conventional metal-organic framework materials for separation in general. Moreover, they show only a very limited uptake capacity, which would lead to a non-economic process.

Even though there are several adsorbent described in the state of the art for the above mentioned separation there is a need for further alternative adsorbents which are easier to prepare, constituted by only one organic linker and efficient for the above mentioned separation.

Thus, an object of the present invention is to provide a metal-organic framework material for the process of separating unbranched hydrocarbons from their branched isomers.

This object is achieved by a process for the separation of at least one unbranched $C_4$-$C_{20}$ hydrocarbon from a fluid mixture containing the unbranched hydrocarbon and at least one branched isomer of the unbranched hydrocarbon, which comprises the step of contacting the fluid mixture with an adsorbent comprising a porous metal organic framework material, which material comprises at least one at least bidentate organic compound coordinately bound to at least one metal ion, to get the unbranched hydrocarbon adsorbed, wherein the at least one at least bidentate organic compound is a monocyclic, bicyclic or polycyclic ring system which is derived from at least one heterocycle selected from the group consisting of pyrrole, alpha-pyridone and gamma-pyridone and has at least two ring nitrogens and is unsubstituted or bears one or more substituents selected independently from the group consisting of halogen, $C_{1-6}$-alkyl, phenyl, $NH_2$, $NH(C_{1-6}$-alkyl), $N(C_{1-6}$-alkyl$)_2$, OH, Ophenyl and $OC_{1-6}$-alkyl, where the substituents $C_{1-6}$-alkyl and phenyl are unsubstituted or bear one or more substituents selected independently from the group consisting of halogen, $NH_2$, $NH(C_{1-6}$-alkyl), $N(C_{1-6}$-alkyl$)_2$, OH, Ophenyl and $OC_{1-6}$-alkyl.

It was founded that the use of specific metal-organic framework materials based on a ring system which is derived from pyrrole or pyridone is useful for the separation mentioned above.

The porous metal-organic framework material used in the process according to the present invention can be prepared by conventional methods as described in U.S. Pat. No. 790,253, M. O'Keeffe et al., J. Sol. State Chem. 152 (2000), 3-20, H. Li et al., Nature 402 (1999), 276, M. Eddaoudi et al., Topics in Catalysis 9, (1999), pages 105 to 111, B. Chen et al., Science 291, (2001), 1021-1023, DE-A-101 11 230, WO-A 2005/049892 and A. C. Sudik et al., J. Am. Chem. Soc. 127 (2005), 7110-7118.

However, preferably the porous metal-organic framework material for the process of the present invention is prepared using an electrochemical procedure as described in WO-A 2007/131955.

Accordingly, the preparation of the porous metal-organic framework material for the process of the present invention involves the anodic oxidation of at least one metal which then enters the reaction medium as cation and reacts with at the least one organic compound to form the porous metal-organic framework material. This framework material can, for example, be separated of by filtration.

Preferably, only one organic compound is used for the build-up of the framework.

The term "electrochemical preparation" as used for the purposes of the present invention refers to a preparative process in which the formation of at least one reaction product in at least one process step is associated with the migration of electric charges or the occurrence of electric potentials.

The term "at least one metal ion" as used for the purposes of the present invention refers to embodiments in which at least one ion of a metal or at least one ion of a first metal and at least one ion of at least one second metal which is different from the first metal is provided by anodic oxidation.

The present invention also comprises embodiments in which at least one ion of at least one metal is provided by anodic oxidation and at least one ion of at least one metal is provided via a metal salt, with the at least one metal in the metal salt and the at least one metal provided as metal ion by means of anodic oxidation being able to be identical or different. The present invention therefore comprises, for example, an embodiment in which the reaction medium comprises one or more different salts of a metal and the metal ion comprised in this salt or in these salts is additionally provided by anodic oxidation of at least one anode comprising this metal. The present invention likewise comprises an embodiment in which the reaction medium comprises one or more different salts of at least one metal and at least one metal different from these metals is provided as metal ion in the reaction medium by means of anodic oxidation.

In a preferred embodiment of the present invention, the at least one metal ion is provided by anodic oxidation of at least one anode comprising this at least one metal and no further metal is provided via a metal salt.

In a further preferred embodiment, the metal organic framework prepared by the process of the invention comprises only one metal.

The present invention accordingly comprises an embodiment in which the at least one anode comprises a single metal or two or more metals and in the case of the anode comprising a single metal, this metal is provided by anodic oxidation and in the case of the anode comprising two or more metals, at least one of these metals is provided by anodic oxidation.

Furthermore, the present invention comprises an embodiment in which at least two anodes are used, with these being able to be identical or different. Each of the at least two anodes can comprise a single metal or two or more metals. It is possible, for example, that two different anodes comprise the same metals but in different proportions. It is likewise possible, for example, in the case of different anodes for a first anode to comprise a first metal and a second anode to comprise a second metal, with the first anode not comprising the second metal and/or the second anode not comprising the first metal.

The metal or the metals are elements of Groups 2 to 15 of the Periodic Table of the Elements. For the purposes of the present invention, preferred metal ions are selected from the group of metals consisting of copper, iron, aluminum, zinc, magnesium, zirconium, titanium, vanadium, molybdenum, tungsten, indium, calcium, strontium, cobalt, nickel, platinum, rhodium, ruthenium, palladium, scandium, yttrium, a lanthanide, manganese and rhenium. Iron, copper, zinc, manganese, nickel and cobalt are more preferred. Particular preference is given to zinc.

A lanthanide comprises La, Ce, Pr, Nd, Pm, Sm, Eu, Gd, Tb, Dy, Ho, Er, Yb and Lu.

As metal ions which are provided in the reaction medium by anodic oxidation, particular mention may be made of $Cu^{2+}$, $Cu^+$, $Ni^{2+}$, $Ni^+$, $Fe^{3+}$, $Fe^{2+}$, $Co^{3+}$, $Co^{2+}$, $Zn^{2+}$, $Mn^{3+}$, $Mn^{2+}$, $Al^{3+}$, $Mg^{2+}$, $Sc^{3+}$, $Y^{3+}$, $Ln^{3+}$, $Re^{3+}$, $V^{3+}$, $In^{3+}$, $Ca^{2+}$, $Sr^{2+}$, $Pt^{2+}$, $TiO^{2+}$, $Ti^{4+}$, $ZrO^{2+}$, $Zr^{4+}$, $Ru^{3+}$, $Ru^{2+}$, $Mo^{3+}$, $W^{3+}$, $Rh^{2+}$, $Rh^+$, $Pd^{2+}$ and $Pd^+$. Particular preference is given to $Zn^{2+}$, $Cu^{2+}$, $Cu^+$, $Fe^{2+}$, $Fe^{3+}$, $Mn^{3+}$, $Mn^{2+}$ $Ni^{2+}$, $Ni^+$, $Co^{3+}$ and $Co^{2+}$. Very particular preference is given to $Zn^{2+}$.

The present invention accordingly also provides a process as described above in which a copper-comprising and/or a nickel-comprising and/or a cobalt-comprising and/or a zinc-comprising and/or an iron-comprising and/or a manganese comprising anode is used as metal ion source.

In a preferred embodiment, the present invention also provides a process as described above in which a zinc-comprising anode is used as metal ion source.

The nature of the anode used in the process of the invention can in principle be chosen freely as long as it is ensured that the at least one metal ion can be provided in the reaction medium by anodic oxidation to allow formation of the porous metal organic framework.

Preference is given to, inter alia, anodes in the form of a rod and/or a ring and/or a disk, for example an annular disk, and/or a plate and/or a tube and/or a bed of loose material and/or a cylinder and/or a cone and/or a frustum of a cone.

In a preferred embodiment, the preparation of a metal-organic framework material for the process of the present invention is carried out using at least one sacrificial anode. The term "sacrificial anode" as used for the purposes of the present invention refers to an anode which is at least partly dissolved during the course of the process of the invention. Embodiments in which at least part of the dissolved anode material is replaced during the course of the process are also encompassed here. This can occur, for example, by at least one fresh anode being introduced into the reaction system or, in a preferred embodiment, an anode being introduced into the reaction system and being fed further into the reaction system either continuously or discontinuously during the course of the preparation process.

Preference is given to using anodes which consist of the at least one metal serving as metal ion source or comprise this at least one metal on at least one suitable support material in the process of the invention.

The geometry of the at least one support material is essentially not subject to any restrictions. It is possible to use, for example, support materials in the form of a woven fabric and/or a sheet and/or a felt and/or a mesh and/or a rod and/or a candle and/or a cone and/or a frustum of a cone and/or a ring and/or a disk and/or a plate and/or a tube and/or a bed of loose material and/or a cylinder.

Possible support materials are, for example, metals such as at least one of the abovementioned metals, alloys such as steels or bronzes or brass, graphite, felt or foams.

Very particular preference is given to anodes which consist of the at least one metal serving as metal ion source.

The nature of the cathode used in the preparation process can in principle be chosen freely as long as it is ensured that the at least one metal ion can be provided in the reaction medium by anodic oxidation.

In a preferred embodiment of the process of the invention, the electrically conductive electrode material of the at least one cathode is selected so that no interfering secondary reaction takes place in the reaction medium. Preferred cathode materials are, inter alia, graphite, copper, zinc, tin, manganese, iron, silver, gold, platinum or alloys such as steels, bronzes or brass.

As preferred combinations of the anode material serving as metal ion source and the electrically conductive cathode material, mention may be made by way of example of:

| Anode | Cathode |
|---|---|
| Zinc | Zinc |
| Zinc | Steel |
| Zinc | Iron |
| Copper | Copper |
| Manganese | Copper |
| Cobalt | Cobalt |
| Iron | Steel |
| Copper | Steel |

The geometry of the at least one cathode is essentially not subject to any restrictions. It is possible to use, for example, cathodes in the form of a rod and/or a ring and/or a disk and/or a plate and/or a tube.

For the purposes of the present invention, it is possible to use essentially any of the types of cell customary in electrochemistry. Very particular preference is given in the process of the invention to an electrolysis cell which is suitable for the use of sacrificial electrodes.

It is in principle possible to use, inter alia, divided cells having, for example, a parallel arrangement of electrodes or candle-shaped electrodes. As separation medium between the cell compartments, it is possible to use, for example, ion-exchange membranes, microporous membranes, diaphragms, filter fabrics composed of materials which do not conduct electrodes, glass frits and/or porous ceramics. Preference is given to using ion-exchange membranes, in particular cation-exchange membranes, and among these preference is in turn given to using membranes which comprise a copolymer of tetrafluorethylene and a perfluorinated monomer comprising sulfonic acid groups.

In a preferred embodiment of the process of the invention, preference is given to using one or more undivided cells.

Very particular preference is given to combinations of geometries of anode and cathode in which the facing sides of the anode and cathode form a gap having a homogeneous thickness.

In an undivided cell, the electrodes are, for example, arranged parallel to one another, with the electrode gap having a homogeneous thickness in the range, for example, from 0.5 mm to 30 mm, preferably in the range from 0.75 mm to 20 mm and particularly preferably in the range from 1 to 10 mm.

In a preferred embodiment, it is possible, for example, to arrange a cathode and an anode parallel to one another so that an electrode gap having a homogeneous thickness in the range from 0.5 to 30 mm, preferably in the range from 1 to 20 mm, more preferably in the range from 5 to 15 mm and particularly preferably the range from 8 to 12 mm, for example in the region of about 10 mm, is formed in the resulting cell. This type of cell will be referred to as a "gap cell".

In a preferred embodiment of the preparation process, the above-described cell is used as a bipolar cell.

Apart from the above-described cell, the electrodes are employed individually or a plurality of them are stacked in a likewise preferred embodiment of the process of the invention. In the latter case, the electrodes are referred to as stacked electrodes which are connected in a bipolar series in what is accordingly referred to as a stacked plate cell. Particularly when the process of the invention is carried out on an industrial scale, preference is given to using at least one pot cell and particularly preferably stacked plate cells connected in series whose in-principle structure is described in DE 195 33 773 A1.

In the preferred embodiment of the stacked plate cell, preference is given, for example, to arranging disks of suitable materials, for example copper disks, parallel to one another so that a gap having a homogeneous thickness in the range from 0.5 to 30 mm, preferably in the range from 0.6 to 20 mm, more preferably in the range from 0.7 to 10 mm, more preferably in the range from 0.8 to 5 mm and in particular in the range from 0.9 to 2 mm, for example in the region of about 1 mm, is in each case formed between the individual disks. Here, the distances between the individual disks can be identical or different, but in a particularly preferred embodiment the distances between the disks are essentially equal. In a further embodiment, the material of a disk of the stacked plate cell can differ from the material of another disk of the stacked plate cell. For example, one disk can be made of graphite and another disk can made of copper, with the copper disk being connected as anode and the graphite disk being connected as cathode.

Furthermore, preference is given for the purposes of the present invention to using, for example, "pencil sharpener" cells as are described, for example, in J. Chaussard et al., J. Appl. Electrochem. 19 (1989) 345-348. Particular preference is given to using pencil sharpener electrodes having rod-shaped, feedable electrodes in the process of the invention.

Cells in which the electrode spacing is less than or equal to 1 mm are referred to as capillary gap cells.

In likewise preferred embodiments of the preparation process, it is possible to use electrolysis cells having, for example, porous electrodes made of beds of metal particles or having, for example, porous electrodes composed of metal meshes or having, for example, electrodes composed of both beds of metal particles and metal meshes.

In a further preferred embodiment, electrolysis cells which have at least one sacrificial anode having a circular disk-shaped cross section and at least one cathode having an annular cross section, with particular preference being given to the diameter of the preferably cylindrical anode being smaller than the internal diameter of the cathode and the anode being located in the cathode in such a way that a gap of homogeneous thickness is formed between the outer surface of the cylindrical anode and the interior surface of the cathode which at least partly surrounds the anode, are used.

It is also possible to reverse the polarity so that the original anode becomes the cathode and the original cathode becomes the anode. In this process variant, it is possible, for example, when suitable electrodes which comprise different metals are chosen, firstly to make available one metal as metal cation by means of anodic oxidation and to make available a further metal in a second step after reversal of the polarity. It is likewise possible to bring about the reversal of polarity by application of AC current.

It is in principle possible to carry out the process batchwise or continuously or in mixed operation. The process is preferably carried out continuously, in particular in at least one flow cell.

The voltages employed in the preparation process can be matched to the respective at least one metal of the at least one anode serving as metal ion source for the porous metal organic framework and/or to the properties of the at least first organic compound and/or, if appropriate, to the properties of the at least one solvent described below and/or, if appropriate, to the properties of the at least one electrolyte salt described below and/or to the properties of the at least one cathodic depolarization compound described below.

In general, the voltages per electrode pair are in the range from 0.5 to 100 V, preferably in the range from 1 to 40 V and particularly preferably in the range from 1.5 to 20 V. Examples of preferred ranges are from about 1.5 to 10 V or from 10 to 20 V or from 20 to 25 V or from 10 to 25 V or from 4 to 20 V or from 4 to 25 V. The voltage can be constant over the course of the process of the invention or can change continuously or discontinuously over the course of the process.

For example, if copper is being oxidized anodically, the voltages are generally in the range from 3 to 20 V, preferably in the range from 3.5 to 15 V and particularly preferably in the range from 4 to 15 V.

The current densities occurring in the preparation of the porous organic framework material are generally in the range from 0.01 to 1000 mA/cm$^2$, preferably in the range from 0.1 to 1000 mA/cm$^2$, more preferably in the range from 0.2 to 200 mA/cm$^2$, more preferably in the range from 0.3 to 100 mA/cm$^2$ and particularly preferably in the range from 0.5 to 50 mA/cm$^2$.

The preparation process is generally carried out at a temperature in the range from 0° C. to the boiling point, preferably in the range from 20° C. to the boiling point, of the respective reaction medium or of the at least one solvent used, preferably under atmospheric pressure. It is likewise possible to carry out the process under superatmospheric pressure, with pressure and temperature preferably being chosen so that the reaction medium is preferably at least partly liquid.

In general, the preparation process is carried out at a pressure in the range from 0.5 to 50 bar, preferably in the range from 1 to 6 bar and particularly preferably at atmospheric pressure.

Depending on the type and physical state of the constituents of the reaction medium, the electrochemical preparation according to the invention of the metal organic framework can in principle also be carried out without an additional solvent. This is, for example, the case particularly when the at least one organic compound in the reaction medium functions as solvent.

It is likewise possible in principle to dispense with a solvent and, for example, carry out the process of the invention in the melt, with at least one constituent of the reaction medium being present in the molten state.

In a preferred embodiment, the reaction medium comprises at least one suitable solvent in addition to the at least one organic compound and, if appropriate, to the at least one electrolyte salt and, if appropriate, to the at least one cathodic depolarization compound. The chemical nature and amount of this at least one solvent can be matched to the at least one organic compound and/or to the at least one electrolyte salt and/or to the at least one cathodic depolarization compound and/or to the at least one metal ion.

Conceivable solvents are in principle all solvents or solvent mixtures in which the starting materials used in the process of the invention can be at least partly dissolved or suspended under the chosen reaction conditions such as pressure and temperature. For the purposes of the present invention, the term "solvent" also comprises solvent mixtures. Examples of solvents used are, inter alia,

- water;
- alcohols having 1, 2, 3 or 4 carbon atoms, e.g. methanol, ethanol, n-propanol, isopropanol, n-butanol, isobutanol, tert-butanol;
- carboxylic acids having 1, 2, 3 or 4 carbon atoms, e.g. formic acid, acetic acid, propionic acid or butanoic acid;
- nitriles such as acetonitrile or cyanobenzene;
- ketones such as acetone;
- at least singularly halogen-substituted lower alkanes such as methyl chloride or 1,2-dichloroethane;
- acid amides such as amides of lower carboxylic acids such as carboxylic acids having 1, 2, 3 or 4 carbon atoms, e.g. amides of formic acid, acetic acid, propionic acid or butanoic acid, for example formamide, dimethylformamide (DMF), diethylformamide (DEF), t-butylformamide, acetamide, dimethylacetamide, diethylacetamide or t-butylacetamide;
- cyclic ethers such as tetrahydrofuran or dioxane;
- N-formylamides or N-acetylamides or symmetrical or unsymmetrical urea derivatives of primary, secondary or cyclic amines such as ethylamine, diethylamine, piperidine or morpholine;
- amines such as ethanolamine, triethylamine or ethylenediamine;
- dimethyl sulfoxide;
- pyridine;
- trialkyl phosphites and phosphates;

and mixtures of two or more of the abovementioned compounds.

The reaction medium preferably comprises an organic solvent which may, if appropriate, be present in admixture with water; the organic solvent particularly preferably comprises an alcohol.

The term "organic solvent" as used above includes both pure organic solvents and organic solvents which comprise small amounts of at least one further compound such as, preferably, water. In this case, the water contents of the abovementioned solvents are in the range up to 1% by weight, preferably in the range up to 0.5% by weight, particularly preferably in the range from 0.01 to 0.5% by weight and very particularly preferably in the range from 0.1 to 0.5% by weight. For the purposes of the present invention, the term "methanol" or "ethanol" or "acetonitrile" or "DMF" or "DEF" also encompasses, for example, a solvent which may in each case particularly preferably comprise water in an amount of from 0.1 to 0.5% by weight. However, the at least one further compound can also be of a different chemical nature. In particular, it does not have to be a customary solvent. Mention may be made by way of example of stabilizers. If a mixture of organic solvents with water is present, it is of course possible for higher proportions of water to be present in the solvent mixture.

Preferred solvents in the preparation process are methanol, ethanol, acetonitrile, DMF, DMAc and DEF or a mixture of two or more of these compounds. Very particular preference is given to methanol, ethanol, DMF, DEF and a mixture of two or more of these compounds as solvent. Methanol is especially preferred.

In a preferred embodiment, at least one protic solvent is used as solvent. This is preferably used when, inter alia, the cathodic formation of hydrogen is to be achieved in order to avoid the redeposition described below on the cathode of the at least one metal ion provided by anodic oxidation.

However, a protic solvent can also be dispensed with for the purposes of the present invention since the at least one organic compound has at least one ring nitrogen to which, at least as represented by a limiting formula, a hydrogen atom is bound and can be split off and reduced.

For example, in the case of methanol being used as solvent, the temperature for the process of the invention under atmospheric pressure is generally in the range from 0 to 90° C., preferably in the range from 0 to 65° C. and particularly preferably in the range from 15 to 65° C.

For example, in the case of ethanol being used as solvent, the temperature in the process of the invention under atmospheric pressure is generally in the range from 0 to 100° C., preferably in the range from 0 to 78° C. and particularly preferably in the range from 25 to 78° C.

In the preparation process, the pH of the reaction medium is set so that it is favorable for the synthesis or the stability or preferably for the synthesis and the stability of the framework. For example, the pH can be set by means of the at least one electrolyte salt.

If the reaction is carried out as a batch reaction, the reaction time is generally in the range up to 30 hours, preferably in the range up to 20 hours, more preferably in the range from 1 to 10 hours and particularly preferably in the range from 1 to 5 hours.

The at least one organic compound is a monocyclic, bicyclic or polycyclic ring system which is derived from at least one heterocycle selected from the group consisting of pyrrole, alpha-pyridone and gamma-pyridone and has at least two ring nitrogens and is unsubstituted or bears one or more substituents selected independently from the group consisting of halogen, $C_{1-6}$-alkyl, phenyl, $NH_2$, $NH(C_{1-6}\text{-alkyl})$, $N(C_{1-6}\text{-alkyl})_2$, OH, Ophenyl and $OC_{1-6}$-alkyl, where the substituents $C_{1-6}$-alkyl and phenyl are unsubstituted or bear one or more substituents selected independently from the group consisting of halogen, $NH_2$, $NH(C_{1-6}\text{-alkyl})$, $N(C_{1-6}\text{-alkyl})_2$, OH, Ophenyl and $OC_{1-6}$-alkyl.

For the purposes of present invention, the term "$C_{1-6}$-alkyl" refers to an alkyl group having from 1 to 6 carbon atoms. Examples are methyl, ethyl, n-propyl, i-propyl, n-butyl, i-butyl, sec-butyl, t-butyl, pentyl, hexyl. Preferred radicals are methyl and ethyl. If a substituted $C_{1-6}$-alkyl radical is present, at least one hydrogen atom is replaced by another substituent.

Furthermore, for the purposes of the present invention, the term "halogen" refers to fluorine, chlorine, bromine or iodine. Preference is given to fluorine and chlorine.

As indicated above, the organic compound is a monocyclic, bicyclic or polycylic ring system which is derived from at least one heterocycle selected from the group consisting of pyrrole, alpha-pyridone and gamma-pyridone. All these three heterocycles have a ring nitrogen which in at least one limiting structure bears a hydrogen atom which can be split off. It is thus possible to deprotonate pyrrole, alpha-pyridone or gamma-pyridone. This forms a negative charge which can at least partly balance the positive charge of the at least one metal ion.

For the purposes of the present invention, the term "derive" means that the monocyclic, bicyclic or polycyclic ring system has at least one substructure which corresponds to pyrrole, alpha-pyridone or gamma-pyridone. Furthermore, two or all three heterocycles can also be present as substructure in the ring system.

For the purposes of the present invention, the term "derive" also means that the three abovementioned heterocycles can occur not in neutral form but, if appropriate, also as anion or cation so that the oxidation can also occur in the presence of these ions.

Furthermore, it should be noted that at least one of the heterocycles which represents a substructure of the ring system is deprotonated during the reaction.

Furthermore, for the purposes of the present invention, the term "derive" means that the substructure of at least one of the three heterocycles can bear substituents and one or more ring carbons can be replaced by a heteroatom.

Of course, the ring system can also be one of the heterocycles pyrrole, alpha-pyridone or gamma-pyridone itself or the ring system can likewise be made up of substructures which are selected exclusively from the group consisting of pyrrole, alpha-pyridone and gamma-pyridone. In this case too, the above-described modifications are possible.

Finally, it should be noted that at least one hydrogen which in at least one limiting structure is not the hydrogen bound to said nitrogen is replaced by a bond by means of which the respective heterocycle is bound to the remainder of the ring system.

If a monocyclic ring system is present, this is derived from pyrrole or alpha-pyridone or gamma-pyridone.

However, the ring system can also be a bicyclic ring system. This is the case when, for example, two rings which are joined to one another via a covalent single bond or via a group R are present in the ring system. Here, one ring has to be derived from pyrrole, alpha-pyridone or gamma-pyridone.

R can be —O—, —NH—, —S—, —N=N— or an aliphatic branched or unbranched saturated or unsaturated hydrocarbon which has from 1 to 4 carbon atoms and may be interrupted by one or more atoms or functional groups selected independently from the group consisting of —O—, —NH—, —S— and —N=N—.

Furthermore, the bicyclic ring system can be a fused ring system.

Examples are, in particular, benzo-fused derivatives derived from pyrrole, alpha-pyridone and gamma-pyridone.

In addition, the bicyclic ring system can be a bridged ring system.

The ring system can likewise be a polycyclic ring system which has, for example, 3, 4 or more rings. Here, the rings can be joined via a covalent single bond and/or a group R and/or be fused and/or be present as a bridged ring system.

The ring system has at least two ring nitrogens. Here, at least one of the two ring nitrogens is that nitrogen which is present in the ring derived from pyrrole, alpha-pyridone or gamma-pyridone. In addition, at least one further ring nitrogen has to be present. If the ring system is one which has more than one ring, the at least second ring nitrogen can also be present in the ring derived from pyrrole, alpha-pyridone or gamma-pyridone or, if the at least one further ring is not derived from one of these three heterocycles, may be located in this ring.

The at least two ring nitrogens are preferably present in one ring of the ring system.

In this case, the ring is derived from pyrazole, imidazole, pyridazin-2-one or pyrimidin-2-one or pyrimidin-4-one. Preference is given to imidazole.

In addition to the two ring nitrogens, further ring nitrogens can be present. For example, the ring system can have 3, 4, 5 or more ring nitrogens.

If more than two ring nitrogens are present, all ring nitrogens can be present in one ring of the ring system or can be distributed over more than one ring up to all rings of the ring system.

If, for example, three ring nitrogens are present, these are also preferably present in the ring which is derived from pyrrole, alpha-pyridone or gamma-pyridone. The resulting substructure of the ring can then be derived, for example, from a triazole, such as 1,2,3-triazole or 1,2,4-triazole.

In addition, the ring system can have further heteroatoms in the ring. These can be, for example, oxygen or sulfur. However, preference is given to no further heteroatoms in addition to nitrogen being present.

If the ring system has more than one ring, this ring can be saturated or unsaturated. The at least one further ring preferably has an at least partially conjugated double bond system or is aromatic in nature.

The ring system can be unsubstituted.

The ring system can also have one or more substituents. If a plurality of substituents are present, these can be identical or different. Preference is given to substituted imidazoles.

The substituents bound to the ring system can be halogen, $C_{1-6}$-alkyl, phenyl, $NH_2$, $NH(C_{1-6}$-alkyl), $N(C_{1-6}$-alkyl$)_2$, OH, Ophenyl or $OC_{1-6}$-alkyl.

If at least one of the abovementioned substituents of the ring system is a $C_{1-6}$-alkyl or phenyl, these can likewise be unsubstituted or bear one or more substituents. When a plurality of substituents are present, it is also possible here for them to be identical or different. These are selected from the group consisting of halogen, $NH_2$, $NH(C_{1-6}$-alkyl), $N(C_{1-6}$-alkyl), $N(C_{1-6}$-alkyl$)_2$, OH, Ophenyl and $OC_{1-6}$-alkyl.

If the group $C_{1-6}$-alkyl occurs more than once, these alkyl groups can be identical or different.

For the purposes of the present invention, the hydroxy or keto group of alpha-pyridone and gamma-pyridone is not counted as a substituent since this group is necessarily present in the ring in order to obtain, at least for one limiting structure, a ring nitrogen bound to hydrogen.

Preference is given to the substituents bound to the ring system having no further substituents.

Preferred substituents bound to the ring system are $C_{1-6}$-alkyl, phenyl, $NH_2$ and OH, $C_{1-6}$-alkyl and $NH_2$ are more preferred. Particular preference is given to $C_{1-6}$-alkyl.

In a further preferred embodiment, the ring system is selected from the group consisting of

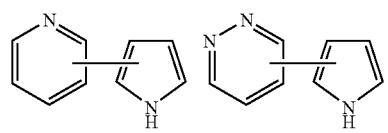

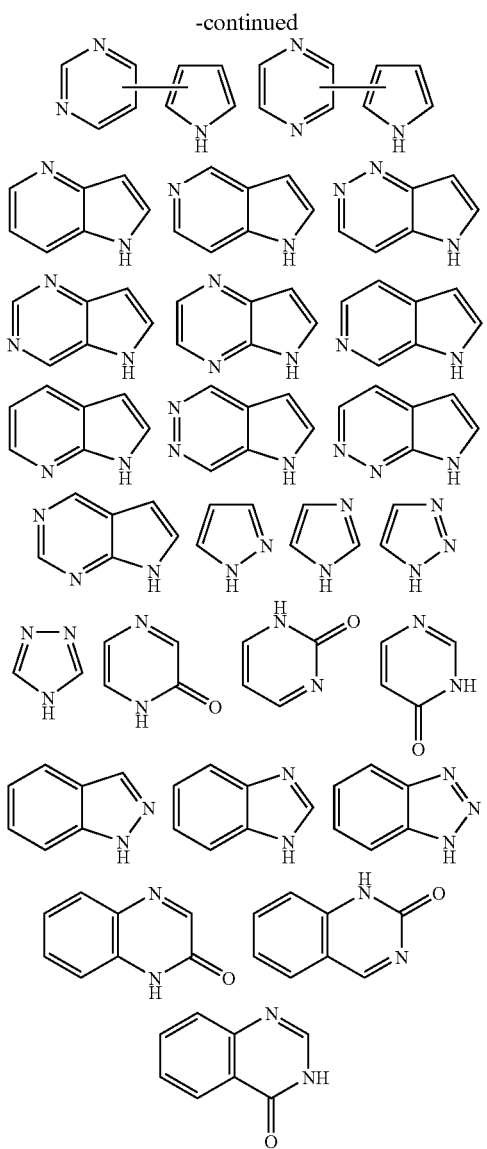

Further preferred ring systems are an imidazole, benzimidazole, triazole, 2-hydroxypyrimidine or 4-hydroxypyrimidine.

The at least one organic compound is very particularly preferably selected from the group consisting of 2-methylimidazole, 2-ethylimidazole, benzimidazole, 1,2,4-triazole, 3-amino-1,2,4-triazole, 3,5-diamino-1,2,4-triazole, 2-hydroxypyrimidine and 4-hydroxypyrimidine and their deprotonated forms.

A particularly useful metal-organic framework material is Zn-2-methylimidazole.

One of the above-described organic compounds can be used in the formation of the porous metal organic framework. However, it is likewise possible to use a plurality of such organic compounds.

However, preference is given to only one of the above-described organic compounds which participates in the formation of the framework being used.

The at least one organic compound is used for the preparation in a concentration which is generally in the range from 0.1 to 30% by weight, preferably in the range from 0.5 to 20% by weight and particularly preferably in the range from 2 to 10% by weight, in each case based on the total weight of the reaction system minus the weight of the anode and the cathode. Accordingly, the term "concentration" in this case comprises both the amount of the at least one organic compound dissolved in the reaction medium and, for example, any amount of the at least one organic compound suspended in the reaction medium.

In a preferred embodiment of the preparation process, the at least one organic compound is added continuously and/or discontinuously as a function of the progress of the electrolysis and in particular as a function of the decomposition of the anode or liberation of the at least one metal ion and/or as a function of the formation of the porous metal organic framework.

It is also possible for further organic compounds whose presence is advantageous for the formation of a desired structure to be added as templates to the electrolyte.

In a particularly preferred embodiment of the preparation process, the reaction medium comprises at least one suitable electrolyte salt. Depending on the at least one organic compound used and/or any solvent used, it is also possible in the process of the invention to carry out the preparation of the porous metal organic framework without any additional electrolyte salt.

The electrolyte salts which can be used in the preparation process are essentially not subject to any restrictions. Preference is given to using, for example, salts of mineral acids, sulfonic acids, phosphonic acids, boronic acids, alkoxysulfonic acids or carboxylic acids or of other acidic compounds such as sulfonamides or imides.

Possible anionic components of the at least one electrolyte salt are accordingly, inter alia, sulfate, monoalkylsulfate such as monomethylsulfate, nitrate, nitrite, sulfite, disulfite, phosphate, hydrogenphosphate, dihydrogenphosphate, diphosphate, triphosphate, phosphite, chloride, chlorate, bromide, bromate, iodide, iodate, carbonate or hydrogen-carbonate.

Possible cation components of the electrolyte salts which can be used according to the invention are, inter alia, alkali metal ions such as $Li^+$, $Na^+$, $K^+$ or $Rb^+$, alkaline earth metal ions such as $Mg^{2+}$, $Ca^{2+}$, $Sr^{2+}$ or $Ba^{2+}$, ammonium ions or phosphonium ions.

As ammonium ions, mention may be made of quaternary ammonium ions and protonated monoamines, diamines and triamines.

Examples of quaternary ammonium ions which are preferably used according to the invention are, inter alia,
- symmetrical ammonium ions such as tetraalkylammonium preferably bearing $C_1$-$C_4$-alkyl, for example methyl, ethyl, n-propyl, isopropyl, n-butyl, isobutyl, tert-butyl, e.g. tetramethylammonium, tetraethylammonium, tetrapropylammonium, tetrabutylammonium, or
- unsymmetrical ammonium ions such as unsymmetrical tetraalkylammonium preferably bearing $C_1$-$C_4$-alkyl, for example methyl, ethyl, n-propyl, isopropyl, n-butyl, isobutyl, tert-butyl, for example methyltributylammonium, or
- ammonium ions bearing at least one aryl such as phenyl or naphthyl or at least one alkaryl such as benzyl or at least one aralkyl and at least one alkyl, preferably $C_1$-$C_4$-alkyl, for example methyl, ethyl, n-propyl, isopropyl, n-butyl, isobutyl, tert-butyl, e.g. aryltrialkylammonium such as benzyltrimethylammonium or benzyltriethylammonium.

In a preferred embodiment, sodium methylsulfate or tributylmethylammonium-methylsulfate is used as electrolyte salt in the preparation process.

In one, inter alia, preferred embodiment of the preparation process, it is possible for compounds which are used for formation of the porous metal organic framework to be introduced into the reaction medium via the cationic and/or anionic component of the at least one electrolyte salt. In particular, at least one organic compound which is comprised in the resulting porous metal organic framework can be introduced via at least one electrolyte salt in the process.

In an embodiment of the preparation process, it is thus possible to introduce the metal ion into the reaction medium via the cationic component of the at least one electrolyte salt in addition to the at least one anode as metal ion source. It is likewise possible for at least one metal ion which is different from the at least one metal ion introduced by means of anodic oxidation in terms of the valence of the cation and/or the type of metal to be introduced into the reaction medium via the cationic component of the at one electrolyte salt.

In the preparation process, the concentration of the at least one electrolyte salt is generally in the range from 0.01 to 10% by weight, preferably in the range from 0.05 to 5% by weight and particularly preferably in the range from 0.1 to 3% by weight, in each case based on the sum of the weights of all electrolyte salts present in the reaction medium and more preferably based on the total weight of the reaction medium without taking into account the anodes and cathodes.

If the preparation process is carried out as a batch process, the reaction medium comprising the starting materials is generally made available first, electric current is subsequently applied and the medium is then circulated by pumping.

If the process is carried out continuously, a substream is generally branched off from the reaction medium, the porous metal organic framework comprised therein is isolated and the mother liquor (the remaining reaction medium) is recirculated.

In a particularly preferred embodiment, the preparation process is carried out so that redeposition on the cathode of the metal ion liberated by anodic oxidation is prevented. According to the invention, this redeposition is, for example, preferably prevented by using a cathode which has a suitable hydrogen overvoltage in a given reaction medium. Such cathodes are, for example, the abovementioned graphite, iron, copper, zinc, tin, manganese, silver, gold, platinum cathodes or cathodes comprising alloys such as steels, bronzes or brass.

Furthermore, the redeposition is, preferably prevented by, for example, using an electrolyte which promotes the cathodic formation of hydrogen in the reaction medium. In this respect, preference is given, inter alia, to an electrolyte which comprises at least one protic solvent. Preferred examples of such solvents have been given above. Particular preference is given here to alcohols, in particular methanol and ethanol.

Furthermore, the redeposition is, preferably prevented by, for example, at least one compound which leads to cathodic depolarization being comprised in the reaction medium. For the purposes of the present invention, a compound which leads to cathodic depolarization is any compound which is reduced at the cathode under given reaction conditions.

As cathodic depolarizers, preference is given, inter alia, to compounds which are hydrodimerized at the cathode. Examples of particularly preferred compounds of this type are acrylonitrile, acrylic esters and maleic esters such as, more preferably, dimethyl maleate.

Further preferred cathodic depolarizers are, inter alia, compounds which comprise at least one carbonyl group which is reduced at the cathode. Examples of such compounds comprising carbonyl groups are, for instance, ketones such as acetone.

As cathodic depolarizers, preference is given, inter alia, to compounds which have at least one nitrogen-oxygen bond, a nitrogen-nitrogen bond and/or a nitrogen-carbon bond which is/are reduced at the cathode. Examples of such compounds are, for instance, compounds having a nitro group, compounds having an azo group, compounds having an azoxy group, oximes, pyridines, imines, nitriles and/or cyanates.

It is also possible in the preparation process to combine at least two of the abovementioned measures for preventing the cathodic redeposition. For example, it is possible to use both an electrolyte which promotes the cathodic formation of hydrogen and an electrode having a suitable hydrogen overvoltage. It is likewise possible both to use an electrolyte which promotes the cathodic formation of hydrogen and to add at least one compound which leads to cathodic depolarization. It is likewise possible both to add at least one compound which leads to cathodic depolarization and to use a cathode having a suitable hydrogen overvoltage. Furthermore, it is possible both to use an electrolyte which promotes the cathodic formation of hydrogen and to use an electrode having a suitable hydrogen overvoltage and also to add at least one compound which leads to cathodic depolarization.

Accordingly, in a preparation process as described above the cathodic redeposition of the at least one metal ion is at least partly prevented by means of at least one of the following measures:

(i) use of an electrolyte which promotes the cathodic formation of hydrogen;
(ii) addition of at least one compound which leads to cathodic depolarization;
(iii) use of a cathode having a suitable hydrogen overvoltage.

As has been indicated above, these measures are not absolutely necessary since hydrogen deposition can in principle be possible and a satisfactory conductivity can in principle be present as a result of the at least one organic compound.

In a particularly preferred embodiment, the preparation process is carried out in the circulation mode. For the purposes of the present invention, this "electrolysis circuit" is any procedure in which at least part of the reaction system present in the electrolysis cell is discharged from the electrolysis cell, if appropriate subjected to at least one intermediate treatment step such as at least one thermal treatment or addition and/or removal of at least one component from the discharged stream and recirculated to the electrolysis cell. For the purposes of the present invention, such an electrolysis circuit is particularly preferably combined with the use of a stacked plate cell, a tube cell or a pencil sharpener cell.

The porous metal organic framework is typically present as a suspension. The framework can be separated off from its mother liquor. This separation can in principle be effected by means of all suitable methods. The framework is preferably separated off by solid-liquid separation, centrifugation, extraction, filtration, membrane filtration, crossflow filtration, diafiltration, ultrafiltration, flocculation using flocculants such as nonionic, cationic and/or anionic auxiliaries, pH shift by addition of additives such as salts, acids or bases, flotation, spray drying, spray granulation or evaporation of the mother liquor at elevated temperatures and/or under reduced pressure and concentration of the solid.

The reaction medium separated off from the porous metal organic framework (mother liquor) can be discarded. However, it is preferably recirculated to the reaction so that it is reused for the oxidation.

The separation can be followed by at least one additional washing step, at least one additional drying step and/or at least one additional calcination step.

If at least one washing step is carried out in the process of the invention, washing is preferably carried out using at least one solvent employed in the synthesis.

If at least one drying step is carried out in the process of the invention, if appropriate after at least one washing step, the framework solid is generally dried at temperatures in the range from 20 to 200° C., preferably in the range from 40 to 120° C. and particularly preferably in the range from 56 to 60° C.

Preference is likewise given to drying under reduced pressure, in which case the temperatures can generally be selected so that the at least one washing liquid is at least partly, preferably essentially completely, removed from the crystalline porous metal organic framework and the framework structure is at the same time not destroyed.

The drying time is generally in the range from 0.1 to 15 hours, preferably in the range from 0.2 to 5 hours and particularly preferably in the range from 0.5 to 1 hour.

The at least one washing step which can be carried out if appropriate and the at least one drying step which can be carried out if appropriate can be followed by at least one calcination step in which the temperatures are preferably selected so that the structure of the framework is not destroyed.

It is possible, for example, for at least one template compound which may, if appropriate, have been used for the electrochemical preparation according to the invention of the framework to be removed at least partly, preferably essentially quantitatively, by, in particular, washing and/or drying and/or calcination.

The process for preparing the porous metal organic framework is typically carried out in water as solvent with addition of a further base. As a result of the preferred use of the organic solvent, it is not necessary to use such a base. Nevertheless, the solvent for the process of the invention can be selected so that it itself is basic, but this is not absolutely necessary for carrying out the process of the invention. In addition, the organic solvent can be present in admixture with water.

It is likewise possible to use a base. However, preference is given to not using any additional base.

In addition to or as an alternative to the abovementioned calcination and/or washing steps, the removal of the at least one organic compound (ligand) from the pores of the porous metal organic framework can be effected by treatment of the framework formed with a further solvent. Here, the ligand is removed in a type of "extraction process" and may, if appropriate, be replaced by a solvent molecule in the framework. This mild method is particularly useful when the ligand is a high-boiling compound.

The treatment preferably takes at least 30 minutes and can typically be carried out for up to 2 days. This can occur at room temperature or elevated temperature. It is preferably carried out at elevated temperature, for example at least 40° C., preferably 60° C. The extraction is more preferably carried out at the boiling point of the solvent used (under reflux).

The treatment can be carried out in a simple vessel by slurrying and stirring of the framework. It is also possible to use extraction apparatuses such as Soxhlet apparatuses, in particular industrial extraction apparatuses.

Solvents which can be used are, for example, $C_{1-6}$-alkanol, dimethyl sulfoxide (DMSO), N,N-dimethylformamide (DMF), N,N-diethylformamide (DEF), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones, such as acetone or acetylacetone, cyclic ketones, such as cyclohexanone or mixtures thereof.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane which has from 1 to 200 carbon atoms and in which one or more up to all hydrogen atoms can be replaced by halogen, preferably chlorine or fluorine, in particular chlorine. Examples are chloroform, dichloromethane, tetrachloromethane, dichloroethane, hexane, heptane, octane and mixtures thereof.

Preference is given to methanol, ethanol, propanol, acetone, MEK and mixtures thereof.

A very particularly preferred extractant is methanol.

The solvent used is preferably water-free.

Independently of its production, the resultant metal-organic framework material is produced in pulverulent or crystalline form. This can be used as such as sorbent in the inventive method alone or together with other sorbents or other materials. Preferably, this is performed as bulk good, in particular in a fixed bed. In addition, the metal-organic framework material can be converted into a shaped body. Preferred methods in this case are rod extrusion or tableting. In the production of shaped bodies, further materials, for example binders, lubricants or other additives, can be added to the metal-organic framework material. Likewise, it is conceivable that mixtures of metal-organic framework material and other adsorbents, for example activated carbon, are produced as shaped bodies, or separately result in shaped bodies which are then used as shaped body mixtures.

Essentially no restrictions exist with respect to the possible geometries of these metal-organic framework materials. For example, those which may be mentioned are, inter alia, pellets, for example disk-shaped pellets, pills, beads, granules, extrudates, for example rods, honeycombs, meshes or hollow bodies.

For production of these shaped bodies, in principle all suitable methods are possible. In particular, preference is given to the following procedures:

Kneading the framework material alone or together with at least one binder and/or at least one pasting agent and/or at least one template compound to obtain a mixture; shaping the resultant mixture by means of at least one suitable method, for example extrusion; optionally washing and/or drying and/or calcining the extrudate; optionally final processing.

Applying the framework material to at least one if appropriate porous support material. The resultant material can then be further processed in accordance with the above-described method to give a shaped body.

Applying the framework material to at least one if appropriate porous substrate.

Kneading and shaping can be performed according to any suitable method, as described, for example, in Ullmanns Enzyklopädie der Technischen Chemie [Ullmann's Encyclopedia of Industrial Chemistry], 4th edition, Volume 2, pp. 313 ff. (1972), the content of which in this respect is incorporated in its entirety by reference into the context of the present application.

For example, preferably, the kneading and/or shaping can be performed by means of a piston press, roller press in the presence or absence of at least one binder material, compounding, pelleting, tableting, extruding, co-extruding, foaming, spinning, coating, granulating, preferably spray-granulating, spraying, spray-drying or a combination of two or more of these methods.

Very particularly, pellets and/or tablets are produced.

The kneading and/or shaping can be performed at elevated temperatures, such as, for example, in the range from room temperature to 300° C., and/or at elevated pressure, such as, for example, in the range from atmospheric pressure up to some hundred bar and/or in a protective gas atmosphere, such as, for example, in the presence of at least one noble gas, nitrogen or a mixture of two or more thereof.

The kneading and/or shaping, according to a further embodiment, is carried out with the addition of at least one binder, as binder, use being able to be made in principle of any chemical compound which imparts the viscosity of the mass to be kneaded and/or shaped desired for the kneading and/or shaping. Therefore, binders, in the context of the present invention, can be both viscosity-increasing, and viscosity-decreasing, compounds.

As binders preferred, inter alia, mention may be made of, for example, aluminum oxide or aluminum-oxide-comprising binders, as are described, for example, in WO 94/29408, silicon dioxide, as described, for example, in EP 0 592 050 A1, mixtures of silicon dioxide and aluminum oxide, as are described, for example, in WO 94/13584, clay minerals, as are described, for example, in JP 03-037156 A, for example montmorillonite, kaolin, bentonite, hallosite, dickite, nacrite and anauxite, alkoxysilanes, as are described, for example, in EP 0 102 544 B1, for example tetraalkoxysilanes, for example tetramethoxysilane, tetraethoxysilane, tetrapropoxysilane, tetrabutoxysilane, or, for example, trialkoxysilanes, for example trimethoxysilane, triethoxysilane, tripropoxysilane, tributoxysilane, alkoxytitanates, for example tetraalkoxytitanates, for example tetramethoxytitanate, tetraethoxytitanate, tetrapropoxytitanate, tetrabutoxytitanate, or, for example, trialkoxytitanates, for example trimethoxytitanate, triethoxytitanate, tripropoxytitanate, tributoxytitanate, alkoxyzirconates, for example tetraalkoxyzirconates, for example tetramethoxyzirconate, tetraethoxyzirconate, tetrapropoxyzirconate, tetrabutoxyzirconate, or, for example, trialkoxyzirconates, for example trimethoxyzirconate, triethoxyzirconate, tripropoxyzirconate, tributoxyzirconate, silica sols, amphiphilic substances and/or graphites. In particular, preference is given to graphite.

As viscosity-increasing compound, use can also be made of, for example, if appropriate in addition to the abovementioned compounds, an organic compound and/or a hydrophilic polymer, for example cellulose or a cellulose derivative, for example methylcellulose and/or a polyacrylate and/or a polymethacrylate and/or a poly(vinyl alcohol) and/or a polyvinylpyrrolidone and/or a polyisobutene and/or a polytetrahydrofuran.

As pasting agents, use can be made of, inter alia, preferably water or at least one alcohol, for example a monoalcohol having 1 to 4 carbon atoms, for example methanol, ethanol, n-propanol, isopropanol, 1-butanol, 2-butanol, 2-methyl-1-propanol or 2-methyl-2-propanol or a mixture of water and at least one of said alcohols or a polyhydric alcohol, for example a glycol, preferably a water-miscible polyhydric alcohol, alone or as a mixture with water and/or at least one of said monohydric alcohols.

Further additives which can be used for kneading and/or shaping are, inter alia, amines or amine derivatives, for example tetraalkylammonium compounds or amino alcohols and carbonate-comprising compounds, for instance calcium carbonate. Such further additives are described, for instance, in EP 0 389 041 A1, EP 0 200 260 A1, or WO 95/19222.

The sequence of the additives such as template compound, binder, pasting agent, viscosity-increasing substance, in the shaping and kneading is in principle not critical. According to a further preferred embodiment, the shaped body obtained according to kneading and/or shaping is subjected to at least one drying which is generally carried out at a temperature in the range from 25 to 300° C., preferably in the range from 50 to 300° C., and particularly preferably in the range from 100 to 300° C. Likewise, it is possible to carry out the drying in a vacuum or under a protective gas atmosphere, or by spray drying.

According to a particularly preferred embodiment, in the context of this drying operation, at least one of the compounds added as additives is at least partially removed from the shaped body.

According to the present invention at least one unbranched $C_4$-$C_{20}$ hydrocarbon is separated from a fluid mixture containing the unbranched hydrocarbon and at least one branched isomer thereof.

Unbranched $C_4$-$C_{20}$ hydrocarbons are alkanes or alkenes, containing one or more C=C-double bonds in the chain having 4 to 20 carbon atoms. Preferred are alkanes.

An unbranched $C_4$-$C_{20}$ alkane is an alkane of formula $H_3C$—$(CH_2)_n$—$CH_3$, wherein n is an integer from 2 to 18. This includes n-butane, n-pentane, n-hexane, n-heptane, n-oktane, n-nonane, n-decane, n-mindecane, n-dodecane as well as the C13-, C14-, C15-, C16-, C17-, C18-, C19-, and C20-n-alkanes.

An unbranched $C_4$-$C_{20}$ alkene can be derived from the respective alkane with one or more C=C double bonds. The term "unbranched $C_4$-$C_{20}$ alkene" includes cis- and trans-forms.

Preferably the at least one unbranched alkane is a $C_4$-$C_{10}$-alkane. These alkanes are n-butane, n-pentane, n-hexane, n-heptane, n-oktane, n-nonane, and n-decane. More preferred are C4, C5 and C8 n-alkanes.

Preferably the at least one unbranched alkane is n-butane.

The fluid mixture can have one of the unbranched hydrocarbons or more than one, e.g. 2, 3, 4, 5, 6, 7, 8, 9, 10 or more of these hydrocarbons.

The corresponding branched isomers have the same number of carbon atoms but at least one at least tertiary carbon atom, which is not an $sp^2$ carbon atom in case of alkenes.

For example the branched isomer of n-butane is isobutane (2-methylpropane). The branched isomers of n-pentane are 2-methylbutane and 2,2-dimethylpropane.

Separating N-alkanes from branched alkanes can be particularly useful for the production of motor fuels. Branched alkanes typically have higher octane ratings than the corresponding n-alkanes. U.S. Pat. No. 3,700,589 describes a process using 5 A zeolite to separate normal from branched chain hydrocarbons. The higher octane fuels earn a premium in the market place because of reduced engine knock and improved performance in engines.

The fluid mixture in the process for the separation according to the present invention can be a liquid or a gas mixture.

In case the fluid mixture is a liquid mixture the process for the separation according to the present invention may be carried out as a so called "simulated moving bed". This is commonly completed in a countercurrent operation in which the feed location through a bed is changed in such a fashion that the adsorbent moves effectively countercurrent to the fluid being used as a desorbent. In said process the desorbent used is chosen such that it is at an intermediate selectivity to the components to be separated. The resulting streams from the process are subsequently passed onto further separation (commonly distillation) to separate the desorbent from the recovered streams.

Preferably, for C4 and C5 hydrocarbons the fluid mixture is a gas mixture. For higher hydrocarbons a liquid phase separation process is preferred.

The contacting of a gas mixture is preferably carried out by continuous adsorption on a fixed bed. In this case the gas mixture is passed through the sorption bed. Further preferably, the continuous adsorption takes place in one or more shaft or tubular reactors, in particular in one or two shaft reactors, at least one reactor being filled with an adsorbent which comprises a porous metal-organic framework material. Reactor cascades are likewise conceivable. A reactor can comprise a part-filling with the porous metal-organic framework material, or a combined bed, for example having additional other adsorbents.

The inventive method is carried out at a partial pressure of the at least one unbranched hydrocarbon which is preferably in the range from 0.5 bar (absolute) and 10 bar (absolute), even more preferred is the range of 0.9 bar and 2.5 bar (absolute).

The temperature of the gas mixture in the contacting with the sorbent which comprises a porous metal-organic framework material can be in a range from 0° C. to 200° C., even more preferred from 5° C. to 150° C., even more preferred from 10° C. to 110° C. In particular the adsorption is carried out at ambient temperature.

The gas mixture is preferably contacted with the sorbent at a gaseous hourly space velocity (GHSV) of 50 l(S.T.P.)/h to 10 000 l(S.T.P.)/h.

The gas mixture can be contacted with the sorbent comprising a porous metal-organic framework material once or repeatedly.

The unbranched hydrocarbon which is separated off and situated on the adsorbent can be desorbed by means of third purge gas under conditions in which the separation (enrichment) is also carried out.

There are further possibilities for desorption without additional purge gas by means of pressure swing adsorption (PSA) including vacuum PSA (VPSA) or temperature swing adsorption (TSA).

Preferably, the desorption takes place with pressure swing adsorption. The manner in which desorption can be carried out is known to those skilled in the art. Instructions for this are found, for example, in Werner Kast "Adsorption aus der Gasphase" [Adsorption from the gas phase], Verlag VCH, Weinheim, 1988.

Preferably the step of contacting is part of a pressure swing adsorption, temperature swing adsorption or combined pressure and temperature swing adsorption process.

Preferably the contacting is carried out for a period of time in the range of 0.5 min to 120 min, more preferred from 0.7 to 60 min. The steps most commonly used in the PSA process would be adsorption followed by equalization, and co current vent to a pressure above the lowest pressure in the cycle. Next a co current pressure reduction to provide a purge gas is completed, followed by a countercurrent depressurization to the lowest pressure in the cycle. Then a purge gas supplied from an earlier step in the cycle is used to sweep the adsorbed material off the bed. After the desorption step is completed the bed is brought back up to pressure with counter current equalization gas and subsequently to adsorption pressure by either feed co currently and/or product gas counter currently.

Another aspect of the present invention is the use of a porous metal organic framework material, which material comprises at least one at least bidentate organic compound coordinately bound to at least one metal ion, wherein the at least one at least bidentate organic compound is a monocyclic, bicyclic or polycyclic ring system which is derived from at least one heterocycle selected from the group consisting of pyrrole, alpha-pyridone and gamma-pyridone and has at least two ring nitrogens and is unsubstituted or bears one or more substituents selected independently from the group consisting of halogen, $C_{1-6}$-alkyl, phenyl, $NH_2$, $NH(C_{1-6}$-alkyl), $N(C_{1-6}$-alkyl$)_2$, OH, Ophenyl and $OC_{1-6}$-alkyl, where the substituents $C_{1-6}$-alkyl and phenyl are unsubstituted or bear one or more substituents selected independently from the group consisting of halogen, $NH_2$, $NH(C_{1-6}$-alkyl), $N(C_{1-6}$-alkyl$)_2$, OH, Ophenyl and $OC_{1-6}$-alkyl, for the separation of at least one unbranched $C_4$-$C_{20}$ hydrocarbon from a fluid mixture containing the unbranched hydrocarbon and at least one branched isomer of the unbranched hydrocarbon.

EXAMPLES

Example 1

Gaschromatographic Separation of n- and i-Butane

Zn-2-Methylimidazol is prepared according to example 1 the international application with the application number PCT/EP2007/054568 and filled into a packed GC column (L50 mm×⅟₁₆" Edelstahlrohr). He (3.8 bar) is used as a carrier gas. The GC is constantly held at 100° C. Small amounts of gases are dosed by the help of a sampling loop and a multiport valve into the He gas stream. The retention time is analyzed by a thermal conductivity detector (TCD).

The retention time for i-butane is 7.00 min, for n-butane 24.26 min. For comparison, the retention time of Ar is 1.16 min.

Example 2

Adsorption Isotherms of n- and i-Butane

Zn-2-Methylimidazol is prepared according to example 1. The uptake is determined gravimetrically by means of a magnetically coupled balance from Rubotherm GmbH, Bochum (DE). Prior to the measurement the sample is activated at 120° C. under vacuum conditions for 5 hours.

FIG. 1 shows the uptake u (in mg/g) as a function of the adsorption pressure p (in mbar) at 31° C. The black diamonds represent the uptake of n-butane, the white squares correspond to i-butane. The difference in the Henry coefficients derived from the initial slope is more than one order of magnitude (~factor 14).

Example 3

Adsorption Isotherms of n- and Neopentane

Figure 2:
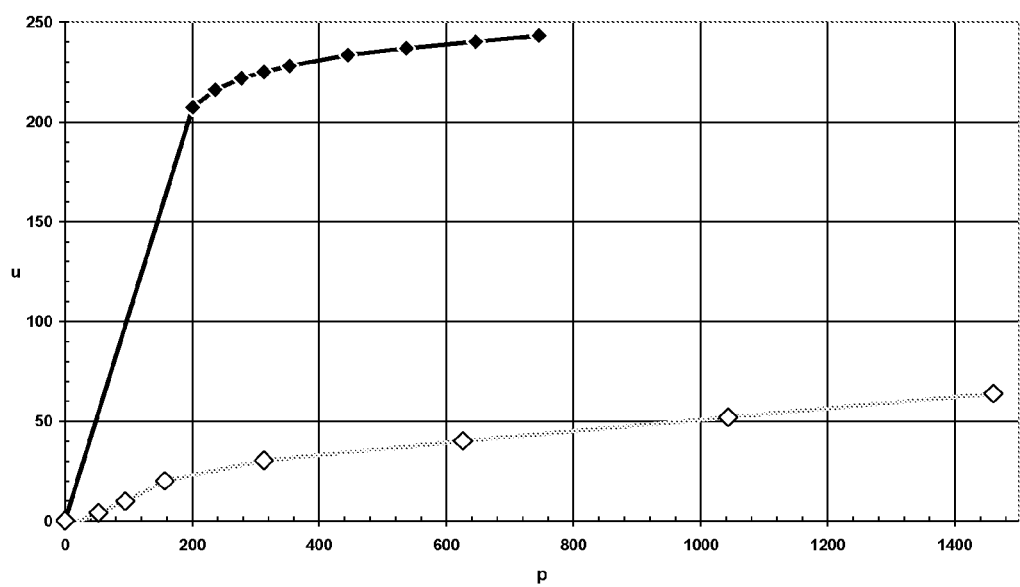

FIG. 2 shows the uptake u of different pentanes (in mg/g) as a function of the absolute adsorption pressure p (in mbar) at 31° C. (otherwise similar conditions as example 1). The black diamonds represent the uptake of n-pentane, the white squares correspond to 2,2-dimethylpropane (neopentane). The difference in the Henry constants is as good as for example 2.

Comparative Example 4

Adsorption Isotherms of n- and i-Butane on 5 A

Figure 3:
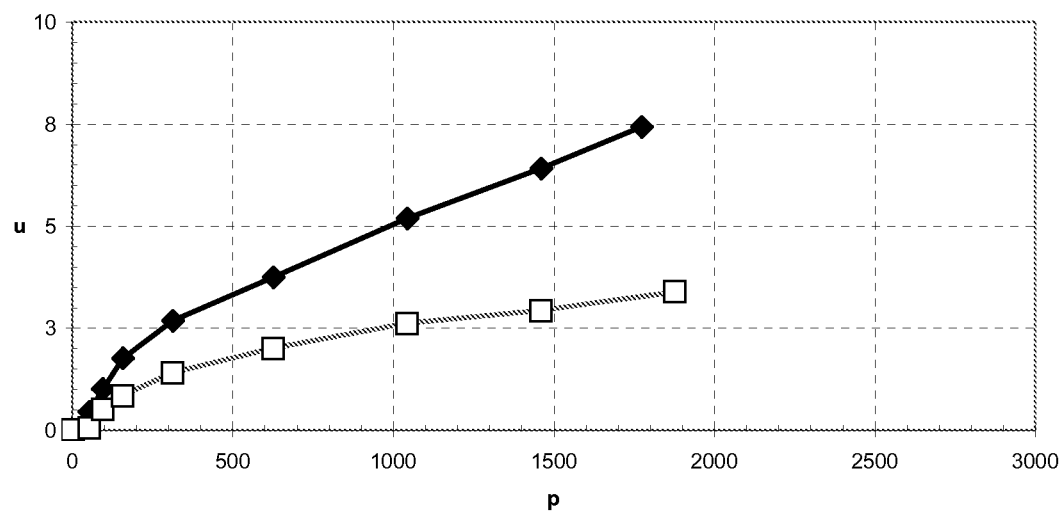

For comparison a commercial 5 A molecular sieve (Carl Roth GmbH+Co. KG, Karlsruhe (DE)). Prior to the experiment the sample is externally activated for 14 hours under vacuum at 300° C. and additionally in-situ under vacuum at 180° C. for 10 hours FIG. 3 shows the uptake u of butanes (in mg/g) as a function of the absolute adsorption pressure p (in mbar) at 31° C. (similar conditions as in example 1). The absolute uptake is much lower than in example 1 and the difference in Henry coefficients is much smaller.

The invention claimed is:

1. A process for the separation of at least one unbranched $C_4$-$C_{20}$ hydrocarbon from a fluid mixture containing the unbranched hydrocarbon and at least one branched isomer of the unbranched hydrocarbon, which comprises contacting the fluid mixture with an adsorbent comprising a porous metal organic framework material, which material adsorbs the unbranched hydrocarbon and comprises at least one at least bidentate organic compound coordinately bound to at least one metal ion, wherein the at least one at least bidentate organic compound is a substituted imidazole ring system comprising one or more substituents selected independently from the group consisting of halogen, $C_{1-6}$-alkyl, phenyl, $NH_2$, $NH(C_{1-6}$-alkyl), $N(C_{1-6}$-alkyl)$_2$, OH, Ophenyl and $OC_{1-6}$-alkyl, where the substituents $C_{1-6}$-alkyl and phenyl are unsubstituted or comprise one or more substituents selected independently from the group consisting of halogen, $NH_2$, $NH(C_{1-6}$-alkyl), $N(C_{1-6}$-alkyl)$_2$, OH, Ophenyl and $OC_{1-6}$-alkyl.

2. The process according to claim 1, wherein the at least one metal ion is an ion of a metal selected from the group consisting of Zn, Cu, Co, Ni, Fe, and Mn.

3. The process according to claim 1, wherein the at least one unbranched hydrocarbon is a $C_4$-$C_{10}$ alkane.

4. The process according to claim 3, wherein the at least one unbranched $C_4$-$C_{10}$ alkane is n-butane.

5. The process according to claim 1, wherein the fluid mixture is a gas mixture.

6. The process according to claim 5, wherein the contacting is carried out at a temperature in the range of 0° C. and 200° C.

7. The process according to claim 5, wherein the contacting is carried out at a partial pressure of the at least unbranched alkane in the range of 0.5 bar (absolute) and 10 bar (absolute).

8. The process according to claim 5, wherein the contacting is carried out for a period of time in the range of 0.5 to 120 min.

9. The process according to claim 5, wherein the of contacting is part of a pressure swing adsorption, temperature swing adsorption or combined pressure and temperature swing adsorption process.

* * * * *